United States Patent [19]
Hammett

[11] Patent Number: 5,181,912
[45] Date of Patent: Jan. 26, 1993

[54] NON-REUSABLE SYRINGE

[76] Inventor: Roy Hammett, 16103 Carden Dr., Odessa, Fla. 33556

[21] Appl. No.: 802,628

[22] Filed: Dec. 5, 1991

[51] Int. Cl.⁵ .............................................. A61M 5/00
[52] U.S. Cl. ..................................... 604/110; 604/228
[58] Field of Search ............... 604/218, 110, 228, 229, 604/187

[56] References Cited

U.S. PATENT DOCUMENTS 4,973,309  11/1990  Sultan .............................. 604/228 X

FOREIGN PATENT DOCUMENTS

2646086  10/1990  France ............................... 604/110
2646087  10/1990  France ............................... 604/110

Primary Examiner—John D. Yasko
Attorney, Agent, or Firm—Dennis H. Lambert

[57] ABSTRACT

A syringe in which a piston is releasably latched to a plunger for reciprocation in a cylindrical barrel, whereby the piston will become disengaged from the plunger upon one cycle of rearward and then forward movement of the plunger and piston in the barrel, followed by subsequent rearward movement of the plunger in the barrel, thus rendering the syringe incapable of reuse. The piston is held to the plunger by latching arms which move to an over-center position between their latched and unlatched positions.

12 Claims, 9 Drawing Sheets

NON-REUSABLE SYRINGE

FIELD OF THE INVENTION

This invention relates generally to hypodermic syringes, and more particularly, to a hypodermic syringe which is rendered inoperative after a single use.

BACKGROUND OF THE INVENTION

It is frequently necessary to use hypodermic syringes for intravenous administration of fluids, or to withdraw fluids from the veins of a person during the course of treatment of an illness, or in routine diagnostic examinations. Hypodermic syringes used for this purpose are generally disposable, and are intended to be discarded after a single use by trained medical personnel.

These syringes are sometimes stolen from hospitals, or from medical equipment suppliers, or are not properly disposed of after being used by authorized personnel, and ultimately come into the possession of drug abusers. Although the medical community has long used disposable syringes a single time and then disposed of the used syringe, intravenous drug abusers consistently use the same syringe over-and-over again and share them with other drug abusers. This practice has led to the rapid spread of the HIV virus and Hepatitis in the drug user population.

Acquired Immune Deficiency Syndrome (AIDS) is now recognized as an epidemic of global proportion. In addition, there is an increasing recognition of a broad spectrum of severe HIV-associated diseases, including pneumonia, endocarditis, and pulmonary tuberculosis, especially among intravenous drug abusers.

Intravenous drug use is believed to account for most AIDS-related diseases in heterosexual men and women. This disease may also be transmitted to the children of infected adults, and to the sex partners of the infected persons, or to others, such as rescue personnel, who may be inadvertently exposed to the blood of the infected person.

As AIDS-related diseases continue to grow, it is becoming increasingly more important to control the means by which these diseases are transmitted, especially among groups associated with intravenous drug abuse. Since the major cause of spread of these diseases is through the repeated and/or shared use of contaminated hypodermic syringes and needles, a significant preventive measure would be the elimination of the ability of intravenous drug abusers to acquire syringes that could be used more than one time.

Examples of some prior art efforts to provide non-reusable syringes are disclosed in U.S. Pat. Nos. 3,478,937, 3,951,146, 4,367,738, 4,391,272, 4,493,703, 4,731,068 and 4,781,684. Most of these patented devices involve some type of catch mechanism which becomes engaged upon full or partial travel of the syringe piston to lock the piston in place and prevent either its withdrawal or its insertion into the syringe barrel. Other devices disclosed in thsese patents include pistons which become separated from the plunger or stem after an operating cycle to eject a fluid from the syringe. For instance, U.S. Pat. Nos. 4,391,272, 4,731,068 and 4,781,684 disclose arrangements in which both some type of catch mechanism and a separable piston and stem structure are used.

All of the prior art devices known to applicant are either excessively complicated and expensive in construction or are not adequately reliable in operation. Further, many prior art devices require either modification of the barrel, or the use of separate collars, adapters or sleeves to connect the piston to the plunger or stem. Moreover, it is possible in some of these devices to reassemble them after use, whereby they may then be repeatedly used.

Accordingly, it would be desirable to have a disposable hypodermic syringe that is reliable in operation, simple and economical in construction, and that is not capable of being reused after a single use.

SUMMARY OF THE INVENTION

The disposable syringe of the invention comprises a conventional cylindrical syringe barrel having a suitable conventional fitting on one end, such as a Luer lock adapter, for attaching a needle, and an open opposite end. A plunger or stem is reciprocable in the barrel and carries a piston on its inner end for developing vacuum or pressure, depending upon the direction of reciprocation of the piston and plunger in the barrel.

In a conventional syringe, the piston is made of rubber and is attached to the end of the plunger so that it will not become displaced from the plunger during use, even though the plunger and piston may be reciprocated many times in the barrel of the syringe. However, in the present invention, the piston is releasably attached to the end of the plunger so that it becomes displaced from the plunger after the plunger and piston are reciprocated through one cycle rearwardly and then forwardly in the barrel. A subsequent reciprocal movement of the plunger rearwardly in the barrel results in the piston becoming separated from the plunger so that it cannot be reattached to the plunger without the use of a special tool used during its manufacture, thus rendering the syringe incapable of further use.

The releasable connection of the piston to the plunger is effected through movable latch arms on the plunger which engage behind naturally biased detents on the piston. The detents are normally clamped between the latch arms and a retaining ring or flange on the plunger. The latch arms are constructed so that when the plunger and piston are withdrawn in the barrel the parts maintain their connected-together position. However, forward movement of the plunger and piston in the barrel results in the latch arms being pivoted outwardly through an over center position away from the detents on the piston, whereby the detents are then enabled to spring outwardly away from the retaining ring on the plunger. Movement of the latch arms through an over center position causes them to be positively retained in their inoperative position. So long as foward movement of the plunger and piston in the barrel continues, the syringe works in the conventional way to discharge material through the forward end of the barrel and thence through the needle and into a vein or other receptacle. However, when reverse movement or withdrawal of the plunger is effected, the detents on the piston become separated from the plunger and the piston therefore remains in place in the barrel, making it impossible to again draw material into the barrel using the plunger and piston.

The piston may be assembled to the plunger only by using a special tool during assembly of the syringe to press the latch arms through their over center position and into locking engagement with the detents on the piston, which are then pressed inwardly against their natural bias and into latching engagement behind the retaining ring on the plunger.

In the present invention the piston is preferably made of a synthetic plastic material, whereas in conventional syringe constructions the piston is normally made of a rubber material. In an alternate construction, however, the piston used in the system of the invention may be made of rubber and still incorporate the novel features of the invention.

BRIEF DESCRIPTION OF THE DRAWINGS

The foregoing and other objects and advantages of the invention will become apparent from the following detailed description when considered in conjunction with the accompanying drawings, wherein like reference characters refer to like parts throughout the several views, and wherein.

DETAILED DESCRIPTION OF THE PREFERRED EMBODIMENTS

Referring more specifically to the drawings, a first form of syringe in accordance with the invention is indicated generally at 10 in FIGS. 1-9 and 11-15. In this form of the invention, a conventional syringe barrel 11 has a forward end 12 with a suitable means, such as a Luer lock adapter 13 for attachment of a needle 14, and an open rearward end 15.

An elongate plunger 16 is reciprocable in the barrel between a forward position inserted fully into the barrel, and a rearward position retracted or withdrawn in the barrel, and has a forward end 17 and rearward end 18. The plunger has a generally H-shaped or I-beam-shaped transverse cross-section, with a central web 19 and oppositely extending flanges 20 and 21 along each side edge of the web. The rearward end of the plunger has a radially enlarged, generally bow-tie-shaped operating flange 22 which may be gripped with the fingers and used to reciprocate the plunger in the barrel.

The forward end of the plunger has a reduced transverse dimension and defines an elongate, forwardly extending attaching post 23 with a plurality of radially outwardly projecting latching arms 24 integrally pivotally connected to the post at hinge areas 25. Four such latching arms are shown in the specific example described herein, but it is contemplated that a different number of arms could be used, if desired. Each arm includes a thickened outer end portion defining detents 26 that are arranged in outwardly spaced, confronting relationship to a radially outwardly projecting retaining ring 27 formed on the post forwardly of the point of attachment of the arms to the post.

A piston 30 is carried on the post 23 at the forward end of the plunger, and in the preferred construction shown in FIGS. 1-9 and 11-15 is made of a synthetic plastic material. This plastic piston has a pair of oppositely axially projecting sealing flanges 31 and 32, each flared radially outwardly and having a radially enlarged sealing bead 33 thereon for effecting a sliding seal with the inner surface of the barrel. Thus, during forward motion of the piston in the barrel, pressure of fluid in the barrel acting under the sealing flange 31 causes that flange to expand radially outwardly, making a tight sliding seal with the inner surface of the barrel. Conversely, rearward movement of the piston in the barrel causes lowered pressure in the forward end of the barrel to pull the sealing flange 32 outwardly to effect a tight sliding seal with the inner surface of the barrel.

Figure 7:
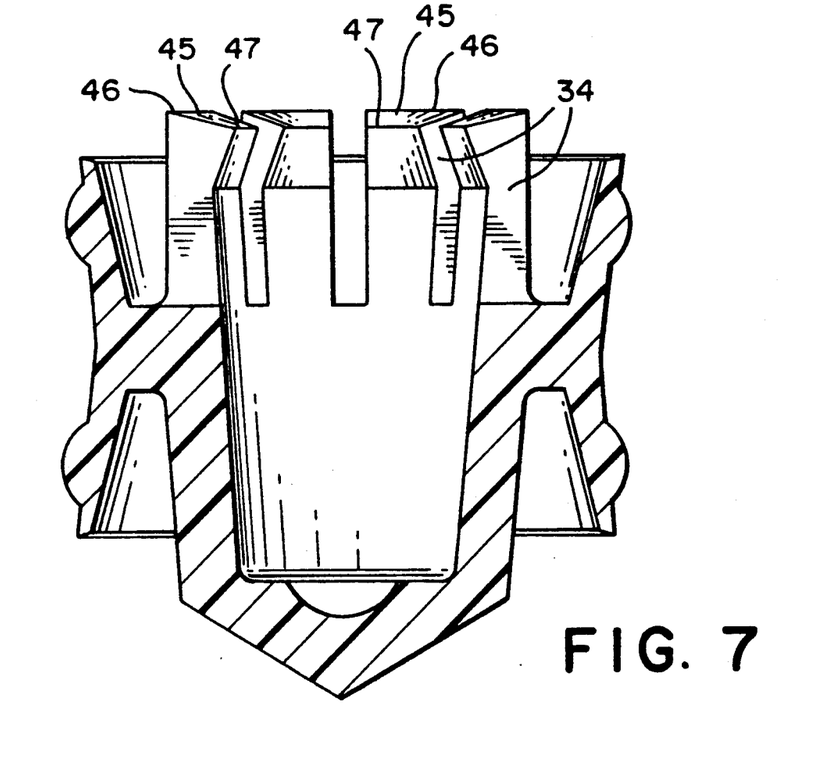
FIG. 7 is a longitudinal sectional view of the piston.
Figure 8:
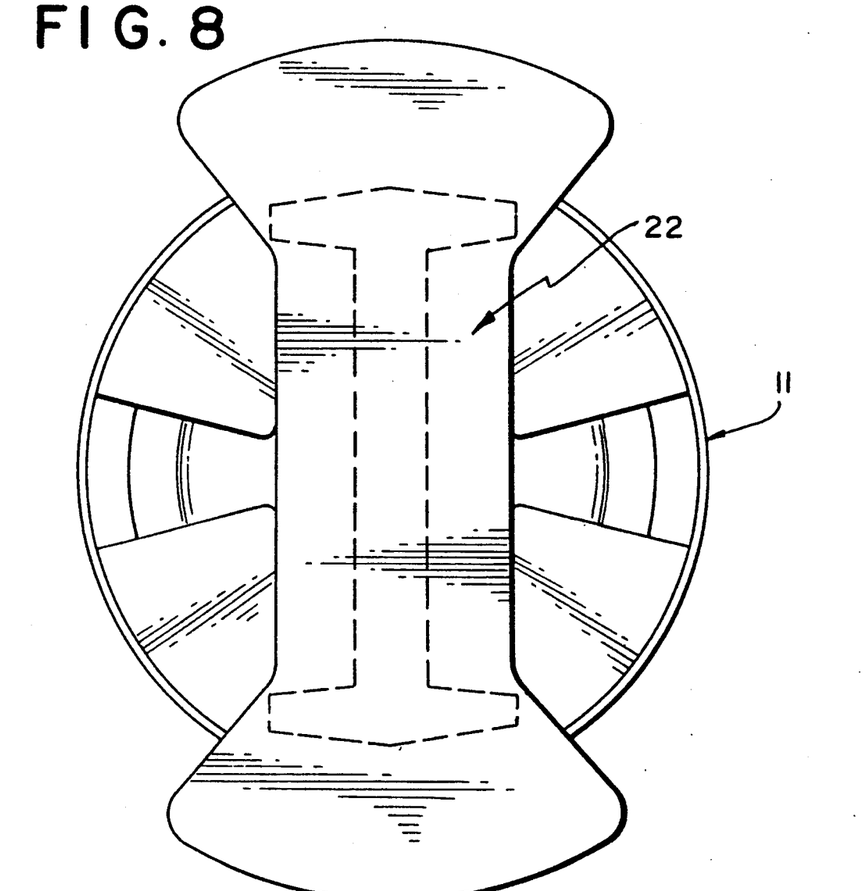
FIG. 8 is a further enlarged end view of the syringe, taken from the plunger end, and showing how the special tool is inserted to pivot the latching arms into their operative position.
Figure 9:
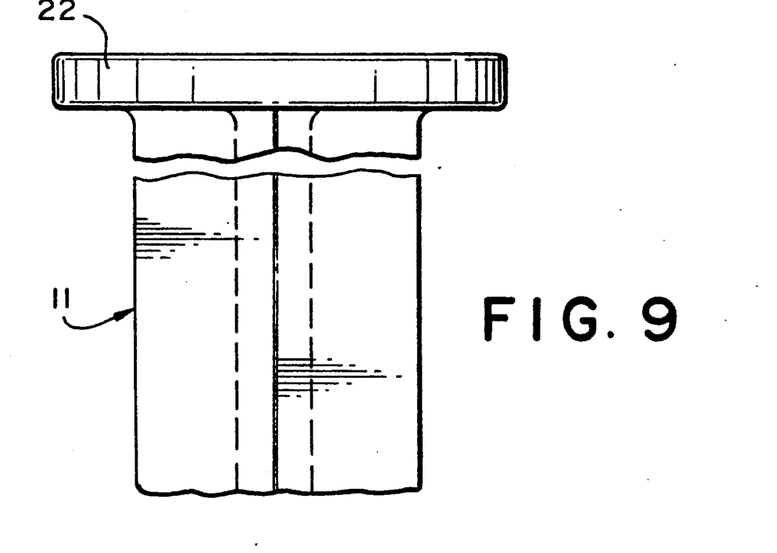
FIG. 9 is an enlarged, fragmentary side view in elevation of the distal end of the plunger.
Figure 14:
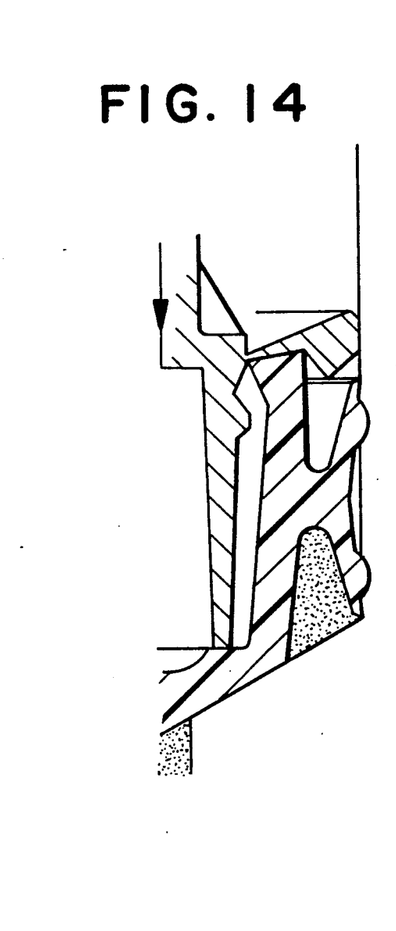

The piston is held on the forward end of the plunger by a plurality of detents 34 on the end of the piston adjacent the plunger, spaced radially inwardly from the sealing flange 32, and clamped between the latching arms 24 and retaining ring 27. These detents are molded with a natural, unbiased position as shown in FIGS. 7 and 14, spaced radially outwardly out of contact with the retaining ring 27, and in the operative position of the invention are held inwardly behind the retaining ring by the latching arms 24.

As seen best in FIGS. 3 and 10-15, the outer ends of the arms 24, the retaining ring 27 and the detents 34 are uniquely shaped to cooperate with one another and with the inner surface of the barrel during reciprocal movement of the plunger in the barrel to either maintain the piston latched to the plunger, or to disengage the piston from the plunger.

Figure 1:
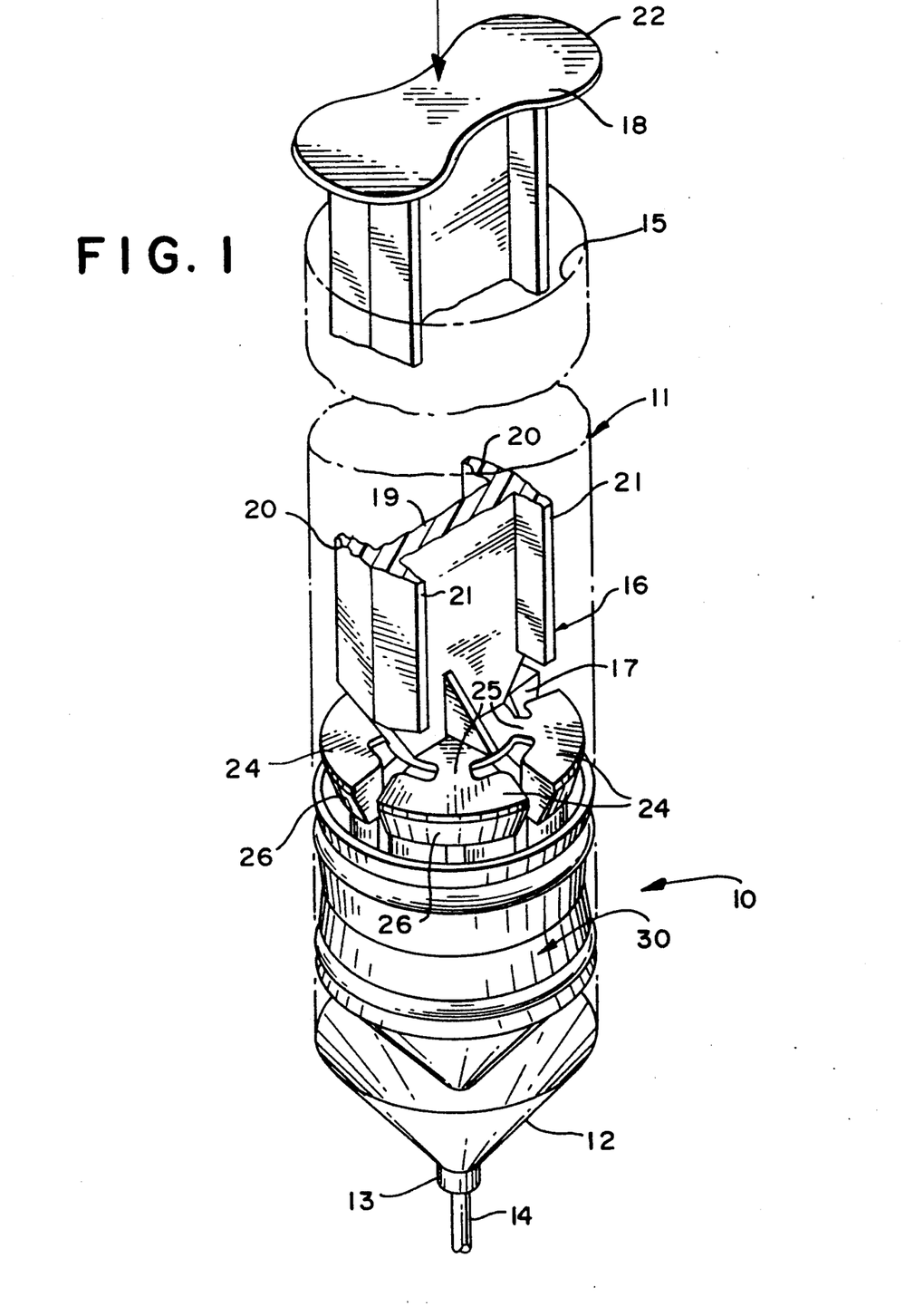
FIG. 1 is a perspective view of a syringe incorporating the features of the invention, with parts broken away to facilitate illustration of the structure.
Figure 2:
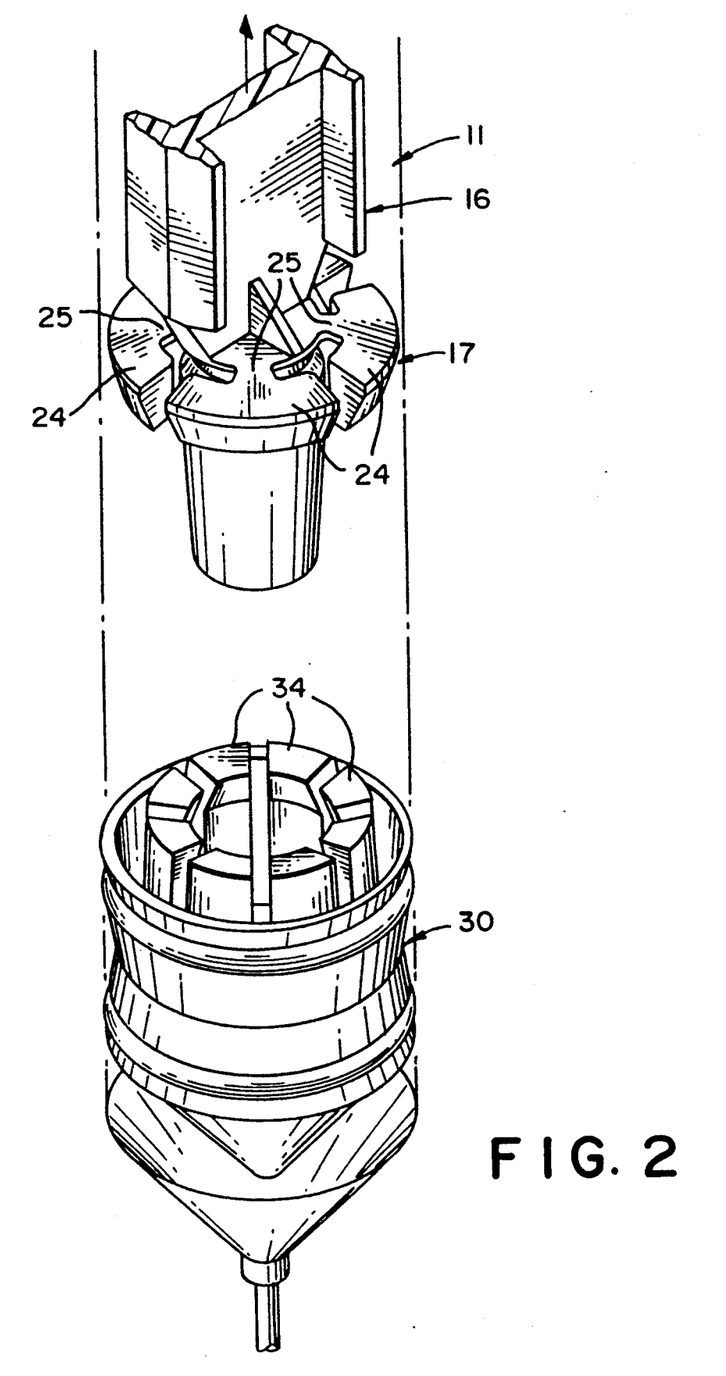
FIG. 2 is a view similar to FIG. 1, with the plunger and piston separated from one another, and showing how the piston remains in the end of the barrel upon retraction of the plunger following dispensing of material from the barrel by forward movement of the plunger and piston therein.
Figure 3:
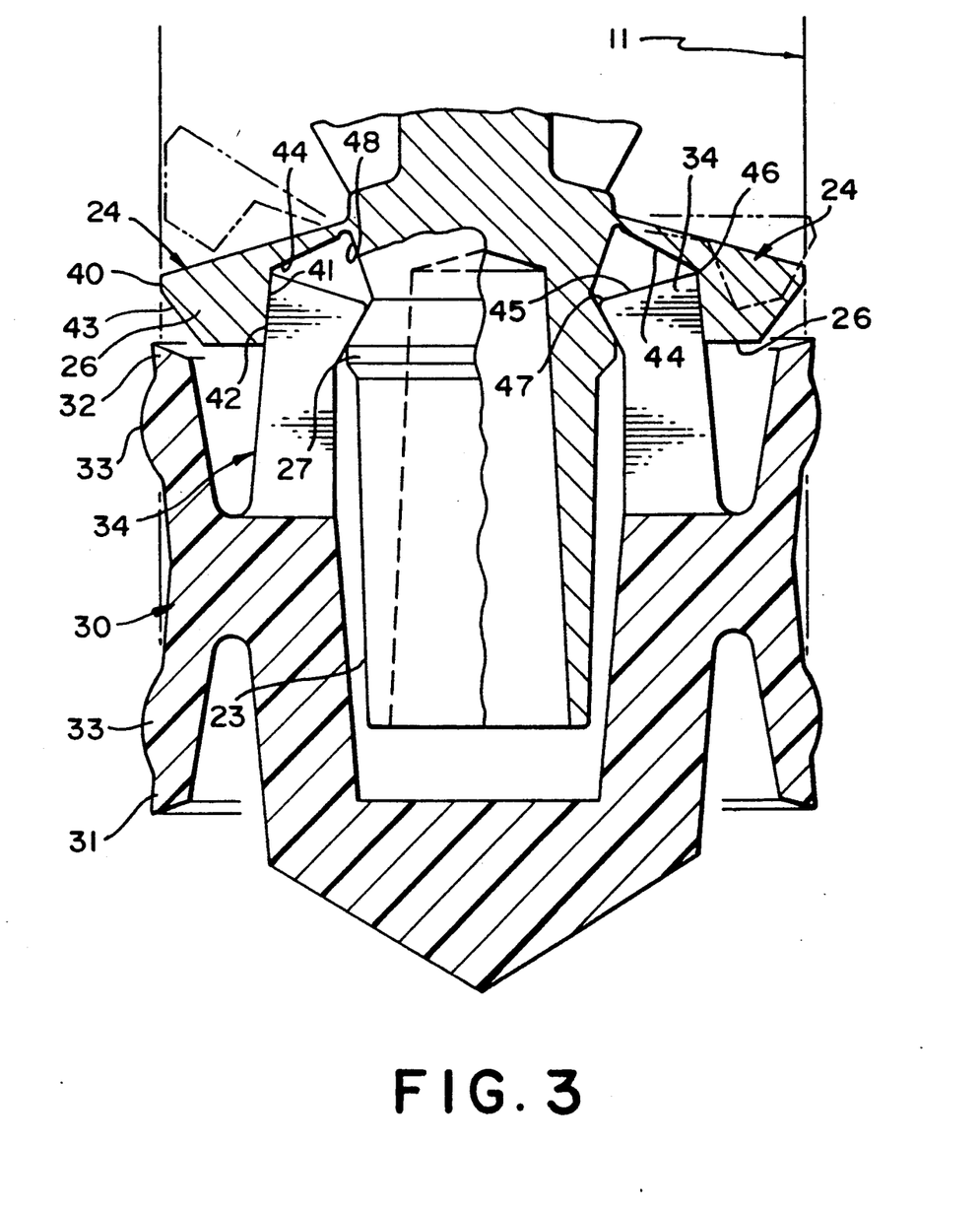
FIG. 3 is a greatly enlarged vertical sectional view of the piston and a portion of the plunger and barrel, illustrating how the latch arms move from their operative to their inoperative positions.
Figure 4:
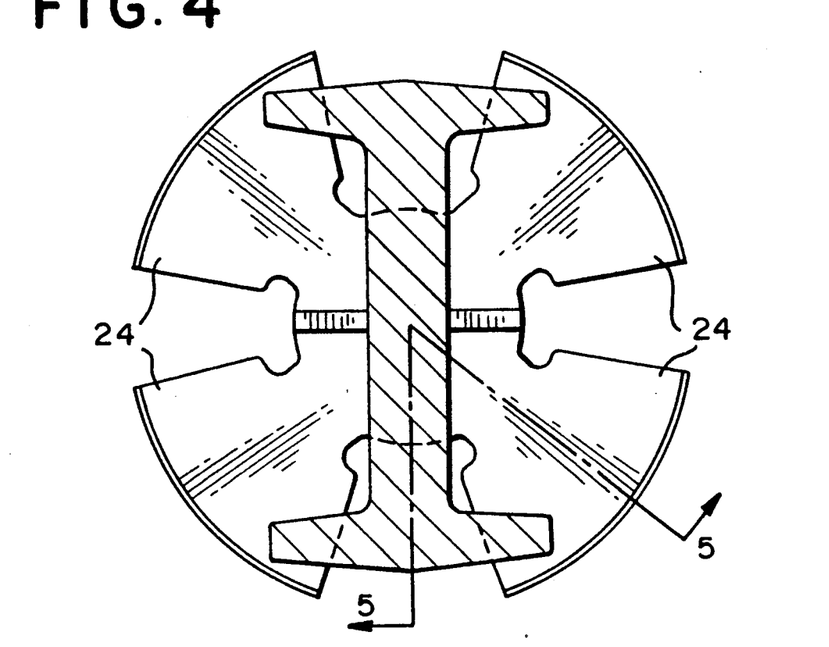
FIG. 4 is a transverse sectional view of the plunger, looking toward the piston end.
Figure 11:
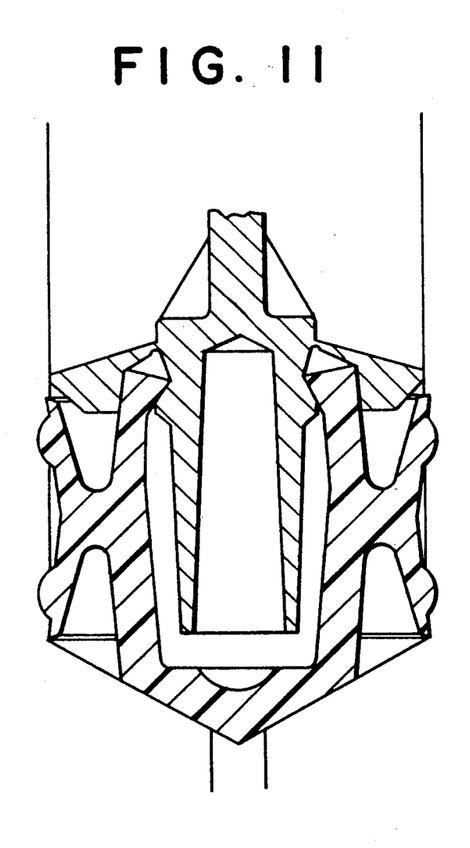
FIGS. 11-15 are fragmentary longitudinal sectional views of the piston and a portion of the plunger and barrel, showing the relationship of the parts during various cycles of movement of the plunger and piston in the barrel.
Figure 12:
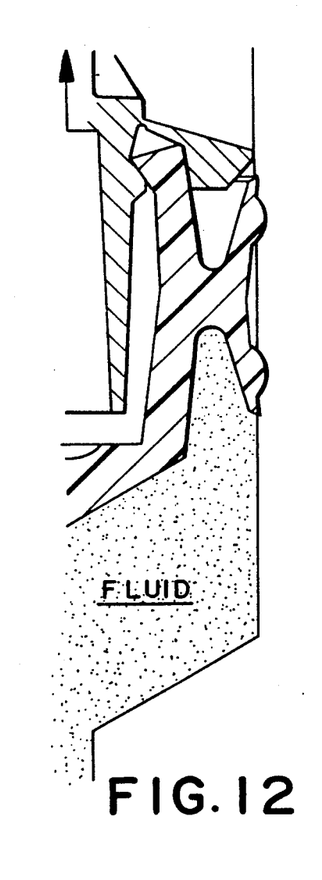

With particular reference to FIGS. 3, 11 and 12, a first of these surfaces 40 defines a relatively narrow annular cylindrical band around the outer perimeter of the latching arms, which is parallel to the inner surface of the barrel and is adapted to slide along the inner barrel surface when the arms are in their normal, operatively latched position with respect to the detents on the piston. Thus, with the piston beginning in its forward-most position at the forward end of the syringe, as seen in FIG. 11, this surface 40 is in parallel, sliding contact with the inner surface of the barrel.

At the same time, a second, latching surface 41 on a radially inner portion of each latching arm is in parallel, mating contact with a complemental latching surface 42 on an upper outer end portion of the detents 34 on the piston to hold the detents inwardly behind the retaining ring 27 and therefore latch the piston to the plunger, as shown in FIGS. 3, 11 and 12.

Figure 13:
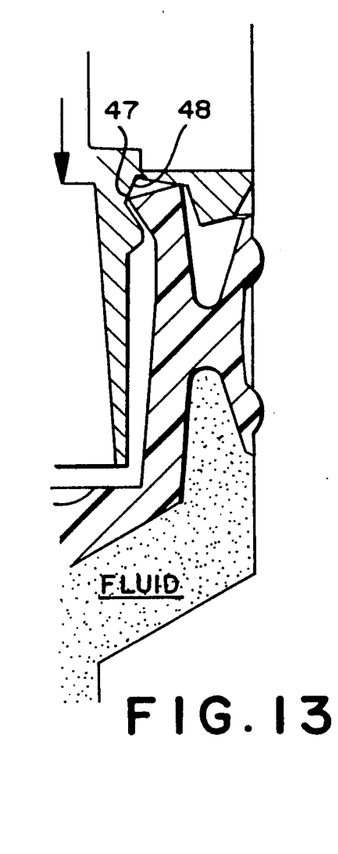
Figure 15:
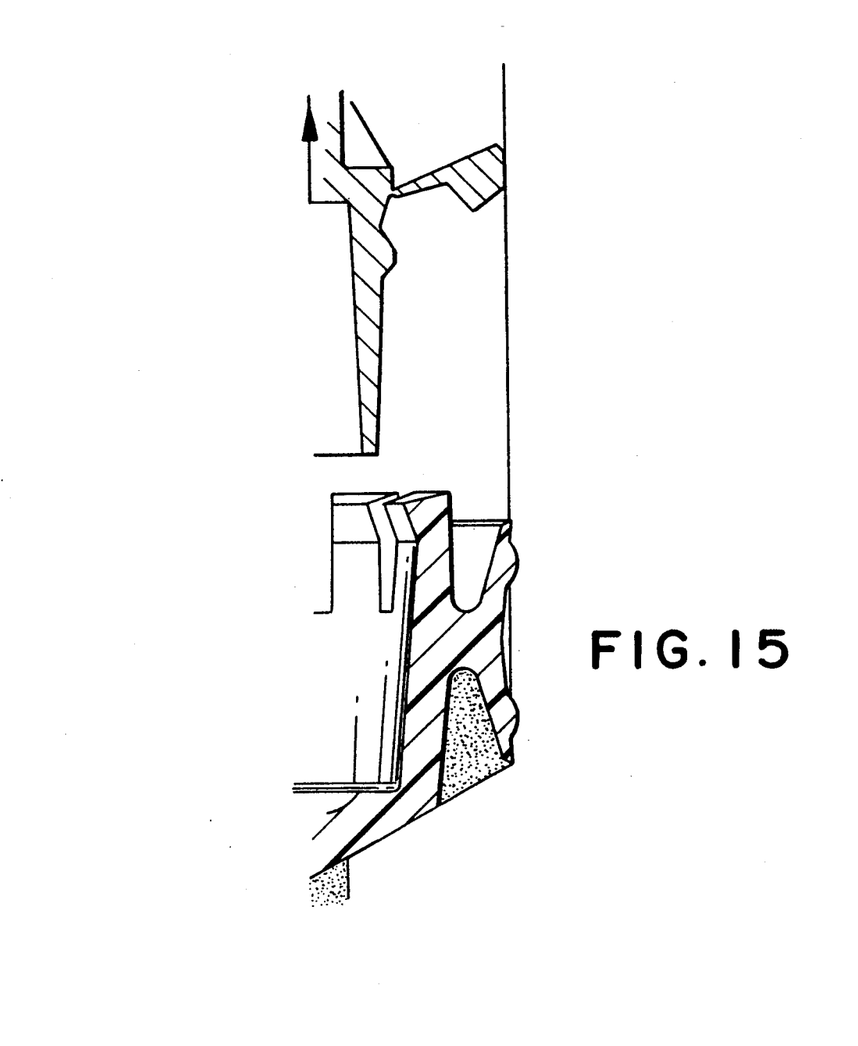

After the piston and plunger have been withdrawn in the barrel, and forward motion thereof is then initiated, the frictional drag between the outer ends of the latching arms and the inner surface of the barrel causes the arms to pivot rearwardly, as depicted in FIG. 13, through an over-center position to a rearwardly flexed inoperative position as shown in FIGS. 14 and 15 and in dot-and-dash lines in the left hand side of FIG. 3. The over center action results from the difference in diameter of the latching arms in comparison with the diameter of the inner surface of the barrel. Thus, when the arms are in their latched, operative position as shown in full lines in FIG. 3, the first surface 40 is on essentially the same diameter as the inner diameter of the barrel, and this surface is in close, sliding contact with the inner surface of the barrel. However, when the arms pivot rearwardly upon forward movement of the piston in the barrel, the outer ends thereof swing through an arc that places the outer ends of the arms on a greater diameter than the diameter of the inner surface of the barrel. Continued forward movement of the piston in the barrel results in the arms pivoting to their unlatched position shown in dot-and-dash lines at the left hand side of FIG. 3, and in full lines in FIGS. 14 and 15. In this position, a third surface 43 on the outer end of the latching arms is in parallel, sliding contact with the inner surface of the barrel. This surface 43 has substantial width in relationship to the first surface 40, and maintains the latching arms in this unlatched position, regardless of the direction of motion of the piston in the cylinder.

With reference to FIGS. 3, 13 and 14, the operating relationship between a fourth surface 44 on the underside of the latching arm and the upper end of the detents 34 will become apparent. The upper end of the detents has a slightly tapered surface 45 that extends between a heel 46 at the radially outermost end thereof, to a nose 47 at the innermost end. Thus, when the plunger and piston have been retracted in the barrel, and forward motion thereof is then initiated as shown in FIGS. 13 and 14, the heel 46 begins pushing upwardly against surface 44 on the latching arm, and, combined with the frictional drag of the outer end of the arm against the inner surface of the barrel, begins upward flexing movement of the arm. Continued movement in this direction, as depicted in FIG. 13, causes the nose 47 to begin sliding upwardly along a fifth surface 48 on the post immediately below the point of attachment of the arms, resulting in radially outward pivoting movement of the detents and continued upward pushing action of the heel against the surface 44. The latching arms are thus pivoted completely through this "over-center" motion to their fully unlatched position shown in FIG. 14, where the end surface 45 on the detents is in parallel contact with the undersurface 44 of the latching arms, securely holding the latching arms in their unlatched position during downward movement of the plunger and piston in the barrel and providing a large contact area between the plunger and piston for pushing the piston forwardly in the barrel.

When the plunger is again retracted in the barrel, as depicted in FIG. 15, the surfaces 43 on the outer ends of the latching arms easily slide along the inner surface of the barrel, whereby the latching arms are maintained in their unlatched position, regardless of the direction of reciprocation of the plunger in the barrel.

During this subsequent withdrawal of the plunger in the barrel, the unlatched piston remains in its forwardmost, previously pushed position in the barrel, as depicted in FIG. 15.

During assembly of the syringe of the invention, the piston is first inserted into the barrel through the open rearward end thereof, and the plunger is next inserted to bring the post and latching arms into the relationship with the piston as shown in FIG. 14. A special tool T is then inserted through the open end of the barrel and into contact with the latching arms, and is used to force the latching arms through their over-center position into the latched position shown in FIG. 11.

Figure 10:
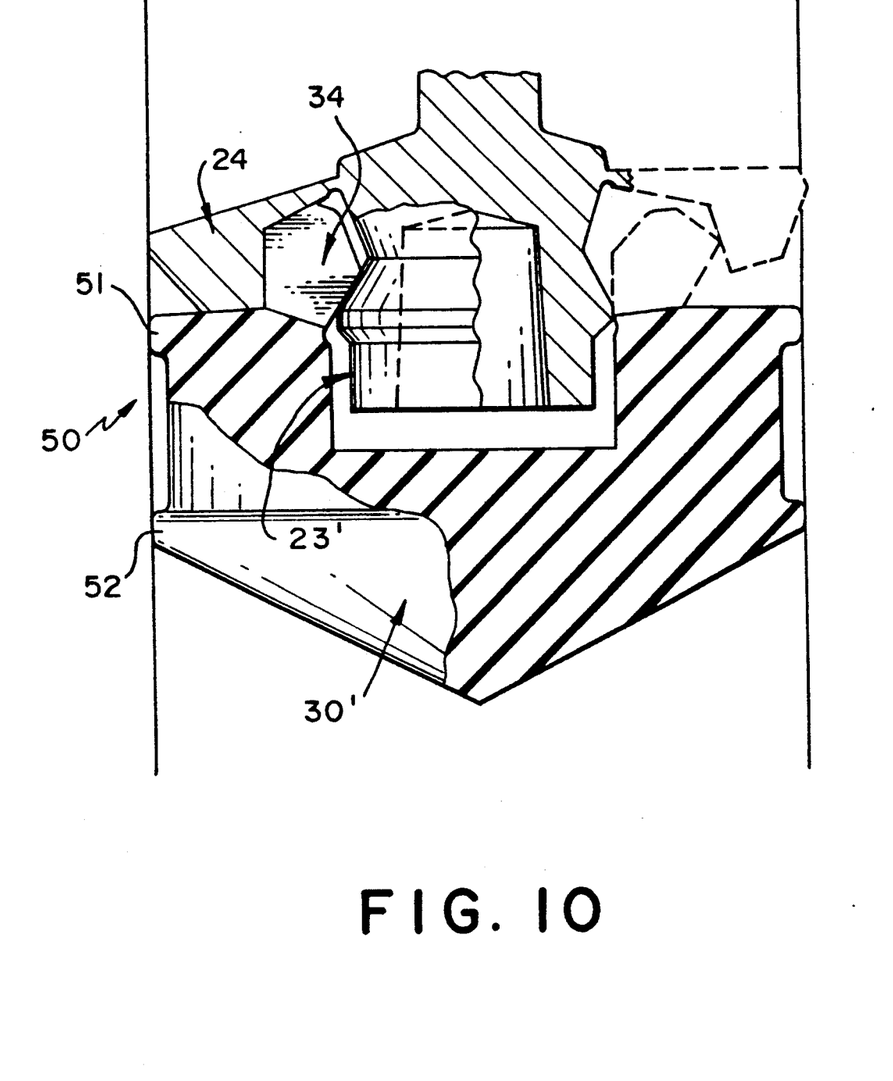
FIG. 10 is a view similar to FIG. 3, showing a modification of the invention in which a rubber piston is used.

A modification of the invention is shown at 50 in FIG. 10, wherein the piston 30'0 is made of rubber rather than plastic as in the previously described form of the invention. The piston itself is constructed differently in the area that it seals with the barrel, but the latching mechanism is substantially identical to that previously described. The sliding seal between the piston and the barrel in this form of the invention is accomplished by a pair of axially spaced sealing rings 51 and 52 on the outer surface of the piston at its forward and rearward ends. In addition, the post 23' is substantially shorter than that previously described. Otherwise, this form of the invention functions identically to the first form.

Figure 5:
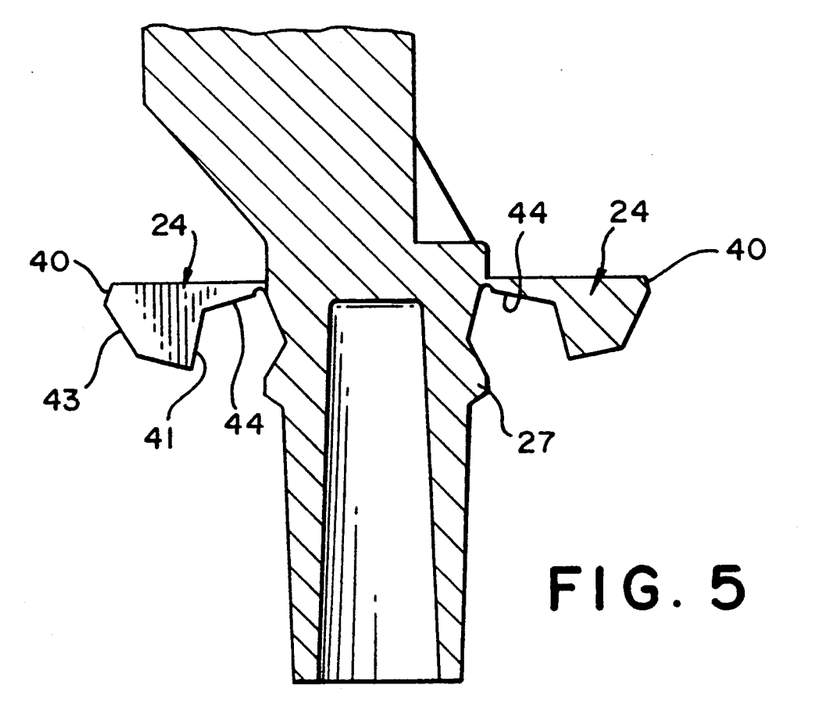
FIG. 5 is a vertical sectional view of the plunger at the forward end thereof, taken along line 5—5, showing the hinge area through which the latch arms are pivoted to the plunger body.
Figure 6:
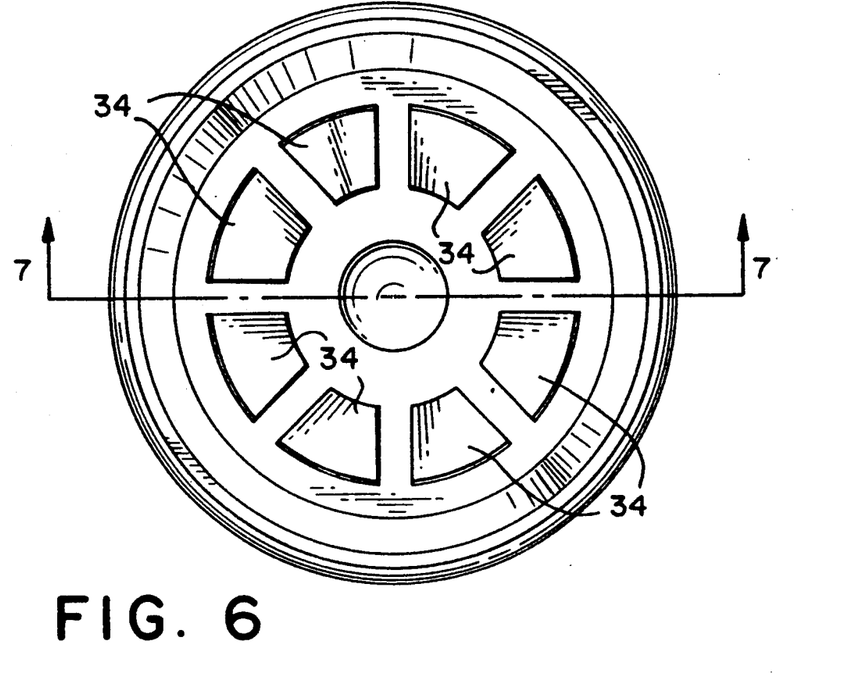
FIG. 6 is a plan view looking down on the piston.

In a specific example of the invention, and with the latching arms in their natural, as-molded position as shown in FIG. 5, the first surface 40 is disposed at an angle of 15° relative to the longitudinal axis of the syringe, the third surface 43 is disposed at an angle of 25° relative to the longitudinal axis, and the fourth surface 44 is inclined 20° with respect to the transverse axis of the syringe. Further, there are four substantially uniformly circumferentially spaced latching arms and eight substantially uniformly circumferentially spaced detents, with each latching arm arranged to press against two of the detents. This can perhaps be best understood by referring to FIGS. 4 and 6.

The syringe of the invention is simple and economical in construction, and does not require any more parts than a conventional syringe, i.e., the barrel, plunger and piston. It is anticipated that the plastic piston version can be produced at a cost comparable with conventional syringes, which use a rubber piston but which do not have the disabling feature of the present invention.

While the invention has been illustrated and described in detail herein, it is to be understood that various modifications may be made therein without departing from the spirit and scope of the invention, as defined by the appended claims.

What is claimed is:

1. A non-reusable syringe, comprising:
    an elongate cylindrical barrel having adapter means on one end for attachment of a needle, and an open other end;
    a two-piece plunger and piston assembly reciprocable in the barrel between a forward position in the barrel and a retracted position, said plunger having a forward end in the barrel and a rearward end accessible exteriorly of the barrel for operating the plunger;
    said piston being carried directly on the forward end of the plunger for effecting a sliding seal with the barrel to draw material into the barrel and discharge it therefrom through said one end upon reciprocating motion of the plunger and piston assembly in the barrel; and releasable latching means on the piston and plunger for latching the piston to the plunger during initial retraction of the plunger and piston in the barrel, and for unlatching the piston from the plunger during forward movement thereof, so that the piston becomes disengaged from the plunger during subsequent retraction of the plunger in the barrel, said latching means including latching arms integral with the forward end of the plunger and extending radially outwardly into sliding contact with an inner surface of the barrel, said latching arms having a first position in latching engagement with detent means on the piston to retain the piston on the plunger, and being movable to a second, over-center, unlatched position releasing the piston from the plunger as the plunger is reciprocated first toward and then away from said one end of the barrel.

2. A syringe as claimed in claim 1, wherein: the latching arms having latching surfaces thereon normally engaged with detents on the piston to urge the detents into latching engagement with a retaining ring integrally formed on the plunger, whereby the detents on the piston are normally gripped between the latching arms and the retaining ring to retain the piston on the plunger.

3. A syringe as claimed in claim 1, wherein: the latching arms are adapted to slide along the inner surface of the barrel in their latched position during rearward movement of the plunger in the barrel, but sliding friction between the latching arms and the barrel during forward movement of the plunger in the barrel causes the arms to move to their over-center, unlatched position.

4. A syringe as claimed in claim 3, wherein: the latching arms have latching surfaces thereon normally engaged with detents on the piston to urge the detents into latching engagement with a retaining ring on the plunger, whereby the detents on the piston are normally gripped between the latching arms and the retaining ring to retain the piston on the plunger.

5. A syringe as claimed in claim 2, wherein: the detents on the piston comprise members that are naturally biased into an unlatched position with respect to the retaining ring on the plunger, and are held in their latched position by the latching arms on the plunger.

6. A syringe as claimed in claim 5, wherein: the piston is made of plastic.

7. A syringe as claimed in claim 1, wherein: the piston is made of plastic.

8. A syringe as claimed in claim 4, wherein: the piston is made of plastic.

9. A syringe as claimed in claim 5, wherein: the piston is made of rubber.

10. A syringe as claimed in claim 1, wherein: the piston is made of rubber.

11. A syringe as claimed in claim 4, wherein: the piston is made of rubber.

12. A syringe as claimed in claim 5, wherein: the detents on the piston are operative to push against the latching arms during forward movement of the plunger and piston in the barrel to facilitate pivoting movement of the latching arms into an unlatched position relative to the detents.

* * * * *